(12) United States Patent
Risch

(10) Patent No.: US 12,383,701 B2
(45) Date of Patent: Aug. 12, 2025

(54) PROTECTIVE DEVICE FOR A CATHETER WITH PROTECTOR REMOVAL FUNCTION

(71) Applicant: BIOTRONIK AG, Buelach (CH)

(72) Inventor: Fabian Risch, Doerflingen (CH)

(73) Assignee: BIOTRONIK AG, Buelach (CH)

( * ) Notice: Subject to any disclaimer, the term of this patent is extended or adjusted under 35 U.S.C. 154(b) by 725 days.

(21) Appl. No.: 17/782,324

(22) PCT Filed: Dec. 1, 2020

(86) PCT No.: PCT/EP2020/084060
§ 371 (c)(1),
(2) Date: Jun. 3, 2022

(87) PCT Pub. No.: WO2021/115840
PCT Pub. Date: Jun. 17, 2021

(65) Prior Publication Data
US 2023/0001133 A1    Jan. 5, 2023

(30) Foreign Application Priority Data
Dec. 12, 2019 (EP) .................................... 19215552

(51) Int. Cl.
*A61M 25/10* (2013.01)
*A61F 2/958* (2013.01)
*A61M 25/00* (2006.01)

(52) U.S. Cl.
CPC .......... *A61M 25/002* (2013.01); *A61F 2/958* (2013.01); *A61F 2002/9583* (2013.01); *A61M 2025/105* (2013.01); *A61M 2025/1081* (2013.01)

(58) Field of Classification Search
CPC .............. A61F 2/966; A61F 2002/9665; A61F 2/9662; A61F 2/9661; A61M 2025/1081
See application file for complete search history.

(56) References Cited

U.S. PATENT DOCUMENTS

| 3,934,721 A | 1/1976 | Juster et al. |
| 5,447,231 A | 9/1995 | Kastenhofer |
| 2011/0152995 A1 | 6/2011 | Mader et al. |

(Continued)

FOREIGN PATENT DOCUMENTS

JP    2015181799 A    10/2015

OTHER PUBLICATIONS

International Search Report from the corresponding International Patent Application No. PCT/EP2020/084060, dated Jan. 28, 2021.

*Primary Examiner* — Deanna K Hall
(74) *Attorney, Agent, or Firm* — Greer, Burns & Crain, Ltd.; Steven P. Fallon

(57) ABSTRACT

A protective device for an elongate catheter carrying a functional element, in particular a stent or a balloon, in particular a balloon coated with an active substance, on a distal end portion of the catheter. The protective device includes a protector configured to be arranged on the distal end portion so that the functional element is surrounded by the protector. A protective sleeve surrounds an interior to receive the catheter together with the protector. The protective sleeve has at least one projection on an inner side of the protective sleeve facing the interior of the protective sleeve. The projection is configured to retain the protector when the catheter together with the protector is arranged in the interior of the protective sleeve and the catheter is withdrawn from the protective sleeve so that the protector is pulled off the distal end portion of the catheter.

14 Claims, 4 Drawing Sheets

(56) References Cited

U.S. PATENT DOCUMENTS

| | | |
|---|---|---|
| 2012/0109281 A1 | 5/2012 | Papp |
| 2014/0110296 A1 | 4/2014 | Terzibashian |
| 2014/0260097 A1 | 9/2014 | Avery et al. |
| 2016/0346072 A1 | 12/2016 | Kawashima |
| 2017/0291011 A1 | 10/2017 | McMenamin et al. |
| 2019/0151605 A1 | 5/2019 | McMenamin et al. |

PROTECTIVE DEVICE FOR A CATHETER WITH PROTECTOR REMOVAL FUNCTION

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2020/084060, which was filed Dec. 1, 2020, which application claimed priority from European Application Serial Number 19215552.1, which was filed Dec. 12, 2019.

FIELD OF THE INVENTION

A field of the invention concerns protective devices for catheters.

BACKGROUND

Such a protective device comprises a protective sleeve, also called a dispenser, which allows the catheter to be transported, the protective sleeve protecting the catheter from abrasive/mechanical influences. A protector cap usually sits on a distal end portion of the catheter and protects a balloon of the catheter and an optional stent placed on it against abrasive/mechanical influences and further ensures that an outer diameter of the distal end portion of the catheter is limited; thus ensuring that the profile of the stent/balloon does not change. Usually, the protector cap is applied to the distal end portion of the catheter during production, more specifically preferably as soon as the stent is placed on the balloon or the balloon (with or without a stent) has been coated with an active substance. The protector cap therefore protects the stent/balloon of the catheter already during production and especially at the end of production when the catheter together with the protector cap is pushed into the protective sleeve.

The protector must be removed before the catheter may be inserted into the body. With conventional protective devices, this is done by manually removing the protector cap, for example by hospital staff at the operating table. The protector cap is usually pulled off manually shortly before the procedure, once the catheter has been removed from the protective sleeve.

However, the manual removal of the protector cap poses the risk of damaging the catheter, especially the stent or balloon, through incorrect manipulation. Furthermore, there is also the risk that the removal of the protector might be forgotten altogether.

FIGS. 1A-1D show components of a known protective device 100 for a catheter 2 that carries a functional element, in particular a stent or an area coated with an active substance 20 (e.g. on a balloon) on a distal end portion 21.

Such a protective device 100 may also include a dispenser ring, which provides mechanical protection for the catheter 2.

The protector 3 of the safety device 100 has various functions. On the one hand, it limits the outer diameter of the distal end portion 21 of the catheter 2 and ensures that the profile of the functional element, in particular of the stent 20 or balloon, does not change. It also provides further mechanical protection for the front part 21 of the catheter 2.

The protector 3 also comprises a cap 30 and an elongate element 35 attached to it in the form of a wire which is inserted into the catheter lumen 22 when the cap 30 is pushed onto the distal end portion 21 of the catheter 2.

In addition, the protective device 100 has a protective sleeve 4 surrounding the stent and/or the balloon on the outside. The protective sleeve 4 may be part of a dispenser ring. The elongate element 35 may protrude from an inner side 36 of the cap 30 facing the interior 31 of the cap 30, in particular from a distal portion 36b of the inner side 36, as shown in FIGS. 1, 3 and 4, and is led out of the interior 31 of the cap 30, in particular through the opening 32 in the cap 30 at the proximal end 30a of the cap 30.

However, there is the disadvantage of the protective device 100 according to FIGS. 1A-1D mentioned above, which is that the protector 3 has to be removed manually after the catheter 2 has been withdrawn from the protective sleeve 4.

SUMMARY OF THE INVENTION

A protective device for an elongate catheter carrying a functional element, in particular a stent or a balloon, in particular a balloon coated with an active substance, on a distal end portion of the catheter. The protective device includes a protector configured to be arranged on the distal end portion so that the functional element is surrounded by the protector. A protective sleeve surrounds an interior to receive the catheter together with the protector. The protective sleeve has at least one projection on an inner side of the protective sleeve facing the interior of the protective sleeve. The projection is configured to retain the protector when the catheter together with the protector is arranged in the interior of the protective sleeve and the catheter is withdrawn from the protective sleeve so that the protector is pulled off the distal end portion of the catheter.

BRIEF DESCRIPTION OF THE DRAWINGS

In the following, embodiments as well as further features and advantages of the invention are to be explained by means of the figures, in which.

DETAILED DESCRIPTION OF THE PREFERRED EMBODIMENTS

Figure 1:
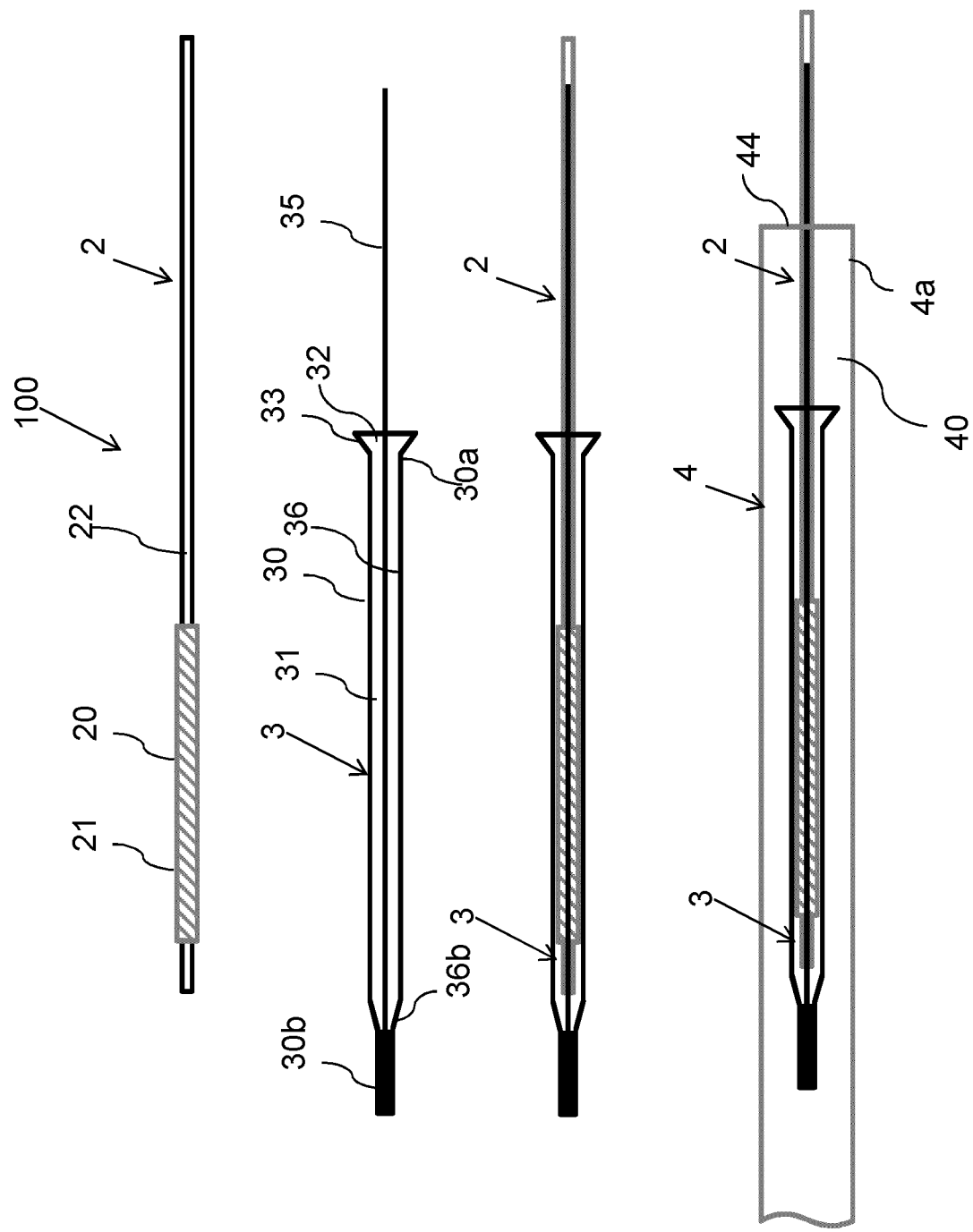
FIGS. 1A-1D (Prior Art) show individual components of a known protective device for a catheter.

A protective device for a catheter according to a preferred embodiment carries a functional element, for example a stent or a balloon, in particular a balloon coated with an active substance, on a distal end portion of the catheter. The protective device includes a protector designed to be arranged on the distal end portion of the catheter so that the functional element, such as the stent or the balloon, is surrounded by the protector. The protective device also includes a protective sleeve surrounding an interior for receiving the catheter and the protector arranged on the distal end portion of the catheter.

According to the invention, it is provided that the protective sleeve has at least one projection on an inner side of the protective sleeve facing the interior of the protective sleeve, which projection is designed to retain the protector when the catheter together with the protector is placed in the interior of the protective sleeve and the catheter is withdrawn from the interior of the protective sleeve so that the protector is pulled off the distal end portion of the catheter.

The invention thus ensures that the protector may be removed in a controlled, reliable manner without damaging the catheter. In addition, the invention eliminates the process step of manually removing the protector, resulting in a corresponding gain in comfort and time. The catheter may be a balloon catheter, for example, in which an optional stent is crimped onto a balloon of the balloon catheter, the optional stent being expandable by means of the balloon (for example for the treatment of a stenosis within the scope of an angioplasty). The balloon catheter, with or without a stent, may also be coated with an active substance.

Within the scope of the present invention, the term distal refers to a part or a component of the catheter or of the protective device which is further along the catheter from a handle of the catheter or from a physician operating the catheter than a corresponding proximal part or a corresponding proximal component of the catheter device which is comparatively closer along the catheter to the handle or closer to the physician.

According to an embodiment of the invention, it is provided that the protector for surrounding the functional element, i.e. the stent or the distal end portion of the catheter, for example with a balloon, comprises a cap having an interior for receiving the distal end portion of the catheter and the stent arranged thereon.

Furthermore, according to an embodiment of the invention, the cap has a funnel-shaped opening at a proximal end of the cap, through which opening the distal end portion of the catheter is insertable into the interior of the cap.

Furthermore, in accordance with one embodiment of the invention, the protector is configured so that when the catheter is withdrawn from the protective sleeve, an edge area of the opening of the cap hits against the projection of the protective sleeve so that the protector or the cap is pulled off the distal end portion of the catheter.

According to one embodiment, the at least one projection may have a rounding so as not to damage the catheter, in particular the functional element, for example in the form of a stent and/or balloon, when the protector is removed.

According to a further embodiment of the invention, it is provided that the protector comprises a holding element, for example in the form of a hook or plate element, arranged at a distal portion of the cap, the holding element being configured to hit against the projection of the protective sleeve when the catheter is withdrawn from the protective sleeve, so that the protector or cap is pulled off the distal end portion of the catheter.

According to another embodiment of the invention, it is provided that the at least one projection forms a rigid element. Furthermore, according to one embodiment, it may be provided that the at least one projection is an integral part of the protective sleeve; for example, is integrally formed on the inside of the protective sleeve or is formed by permanent deformation of the protective sleeve.

According to a further embodiment of the invention, it is provided that the at least one projection is formed by a movable wing, which is in particular designed to be moved by the protector from a disengaged position to an engaged position when the catheter is inserted and to return automatically to the disengaged position after passing the protector, wherein in the disengaged position the protector (in particular said edge area or hook-shaped element) may strike against the projection when the catheter is withdrawn from the interior of the protective sleeve.

Furthermore, according to an embodiment of the invention, it is provided that the at least one projection is arranged in a proximal portion of the protective sleeve, the proximal portion having an opening of the protective sleeve through which the catheter may be inserted into the interior of the protective sleeve with the protector in front.

Furthermore, according to one embodiment of the invention, it is provided that the protective sleeve is arranged in a ring shape. In this case, the protective sleeve may have a number of turns. In this way, even a relatively long catheter may be brought to a format that is easier to handle and more suitable for the storage and transport of the catheter. The protective sleeve may be made of plastic, for example, or may be at least partially made of plastic.

In addition, according to an embodiment of the invention, a card may be attached to the protective sleeve, on which card information regarding the catheter is reproduced (so-called compliance data card).

In one embodiment, the protector of the protective device, in particular the cap, is designed to limit the outer diameter of the functional element, for example in the form of a stent or the balloon, so that a profile of the functional element does not change. Furthermore, the protector is designed to protect the stent and/or the balloon, in particular a balloon coated with an active substance, against abrasive/mechanical effects.

Furthermore, according to one embodiment of the invention, the protector comprises an elongate element, in particular in the form of a wire which is designed to be disposed in a lumen of the catheter when the protector, in particular the cap, is disposed as intended on the distal end portion of the catheter.

According to one embodiment of the invention, the elongate element is intended to project from an inner side of the cap facing the interior of the cap, in particular from a distal portion of the inner side of the cap.

Preferably the elongate element protrudes through the opening of the cap from the interior of the cap.

A further aspect of the invention relates to an arrangement comprising a protective device according to the invention as well as a catheter, wherein the catheter carries a functional element, in particular a stent or a balloon, in particular a balloon coated with an active substance, on a distal end portion of the catheter, wherein the protector is arranged on the distal end portion of the catheter so that the functional element, in particular the stent or the balloon, is surrounded by the protector. The protective sleeve has, on the inner side of the protective sleeve facing the interior of the sleeve, the said at least one projection designed to retain the protector when the catheter is withdrawn from the sleeve, so that the protector is pulled off from the distal end portion of the catheter.

Figure 4:
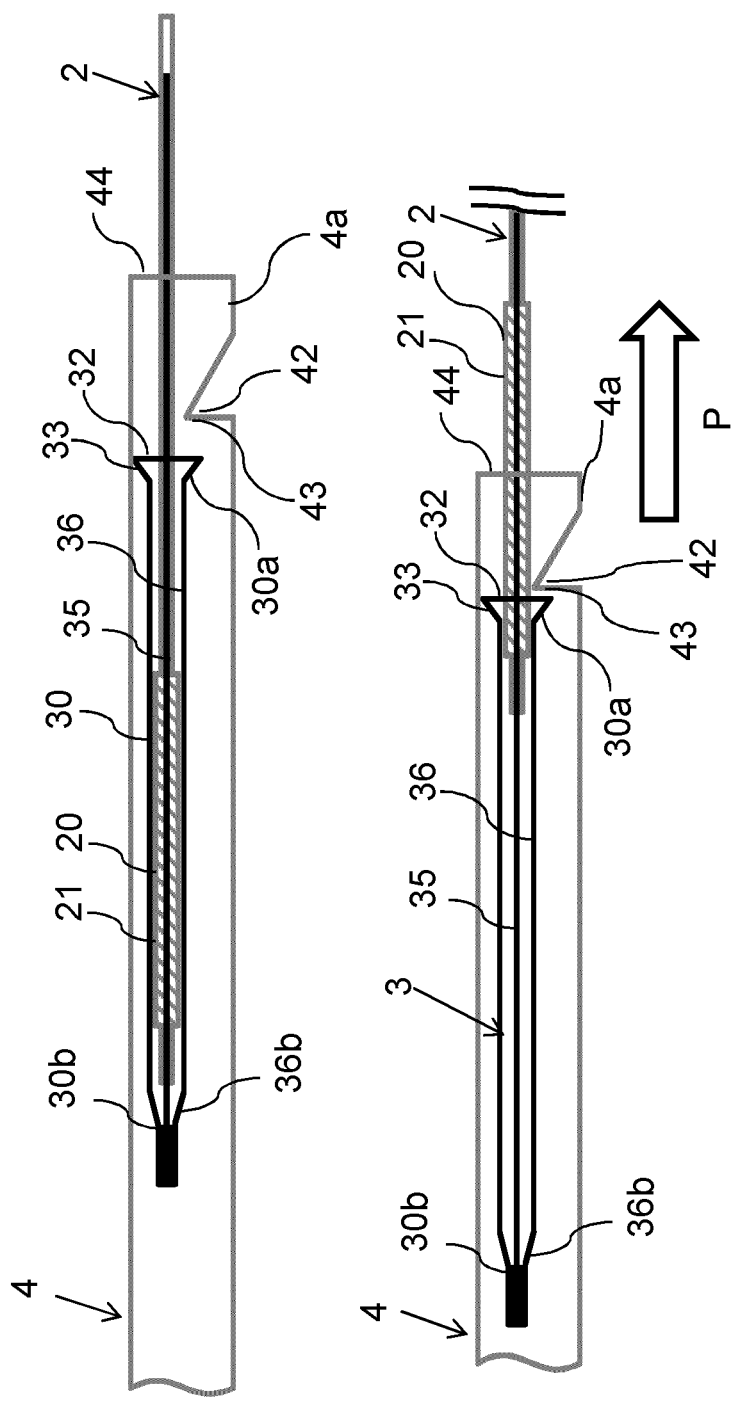
FIGS. 4A-4B show an alternative embodiment of a protective device according to the invention, wherein a protector of the protective device is removed from a distal end portion of the catheter by means of an edge area of an opening of a protector cap.

FIGS. 4A-4B show a protective sleeve 4 and cap 30 that are adapted to avoid manual removal of the protector 3. It is then provided that the protective sleeve 4 is given (in this particular example) a projection 42, or rather a constriction in the interior 40, so that the protector 3 remains attached to it when the catheter 2 is withdrawn from the interior 40 of the protective sleeve 4 in a proximal direction P.

For the mentioned interaction of the protector 3 with the projection 42, for example, a funnel-shaped edge area 33 of the opening 32 of the cap 30 of the protector 3 may be used, as shown in FIGS. 4A-4B. In this case, the projection 42 may have a rounding 43, for example, to avoid the risk of damaging the catheter 2 when removing the protector 3.

Figure 3:
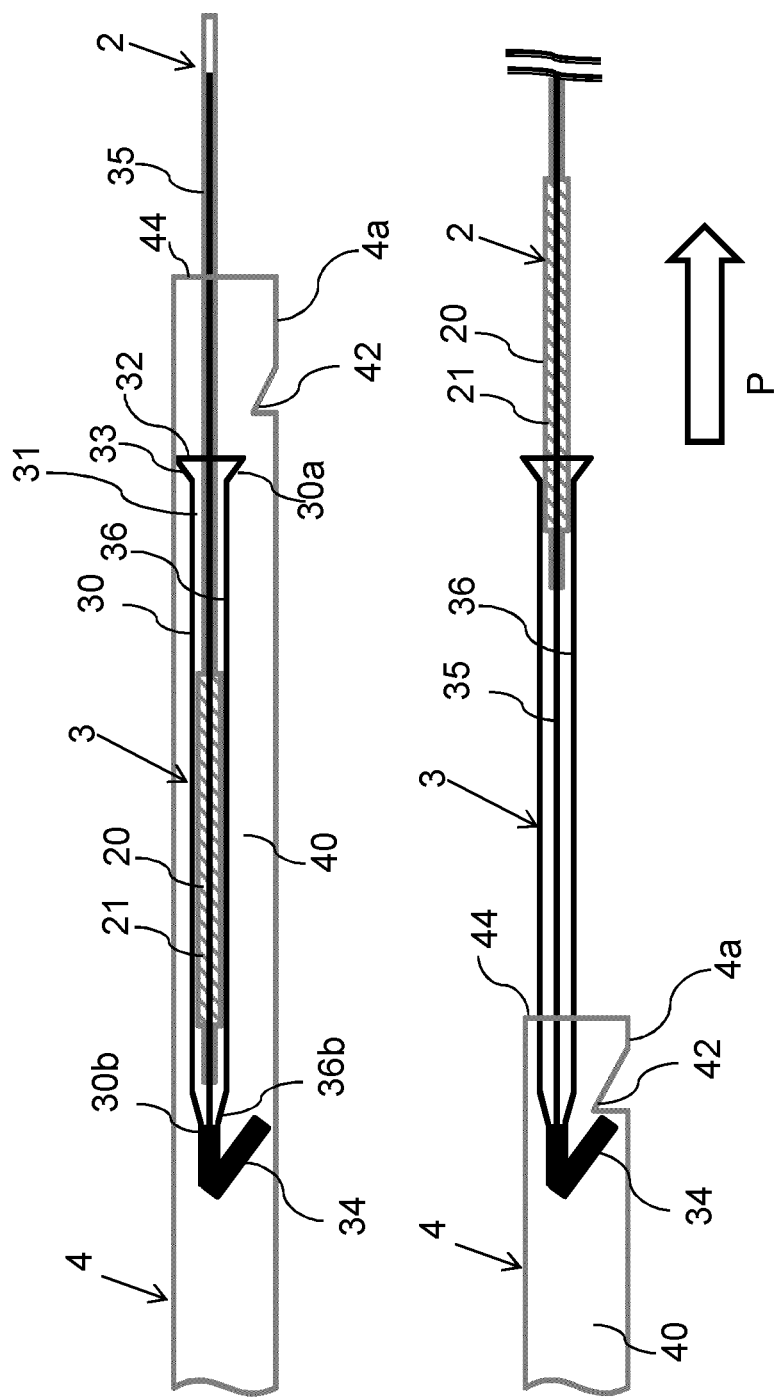
FIGS. 3A-3B show an embodiment of a protective device according to the invention, wherein a protector of the protective device is withdrawn from a distal end portion of the catheter by means of a hook-shaped element.

A preferred further embodiment of the invention is shown in FIGS. 3A-3B. According to this embodiment, it is provided that the protector 3 has a holding element (here a hook element) 34 at the distal end 30b of the cap 30, wherein the holding element 34 is configured to hit against the projection 42 of the protective sleeve 4 when the catheter 2 is withdrawn from the interior 40 of the protective sleeve, so that the protector 3 or the cap 30 is pulled off the distal end portion 21 of the catheter 2.

In both embodiments (FIGS. 3A-4B) the projection 42 is preferably located in a proximal portion 4a of the protective sleeve 4, wherein the proximal portion 4a also contains the opening 44 of the protective sleeve 4, through which the catheter 2 is insertable into the interior 40 of the protective sleeve 4 with the protector 3 in front.

The constriction or projection 42 of the protective sleeve 4 may be prefabricated, may represent an additional component, or may be inserted into the protective sleeve 42 subsequently, after the catheter 2 has been fitted (for example thermally and/or mechanically).

However, the projection 42 may also be formed by a movable wing designed to move from a disengaged position to an engaged position by the protector 3 when the catheter 2 is inserted into the interior 40 of the protective sleeve 4 and to return to the disengaged position after passing the protector 3, which allows the protector 3 to be stripped off when the catheter 2 is withdrawn from the interior 40 of the protective sleeve 4.

Figure 2:
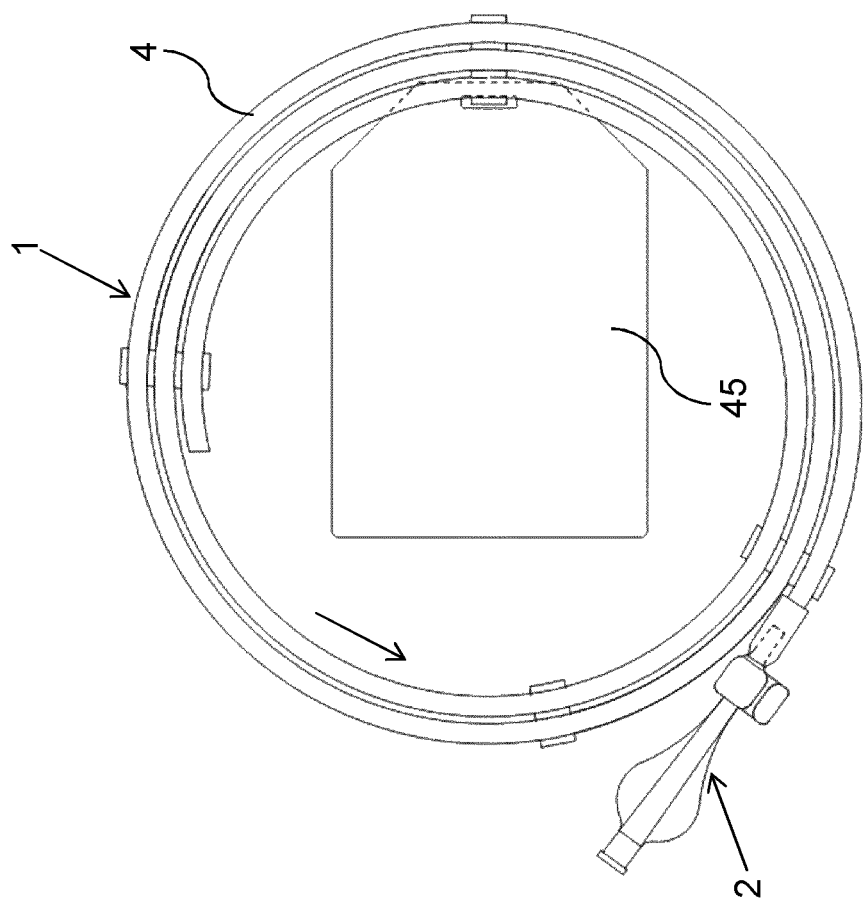
FIG. 2 shows an embodiment of a protective device according to the invention with a rolled up protective sleeve.

As shown in FIG. 2, in both embodiments of the invention (FIGS. 3A-4B the protective sleeve 4 may be arranged and fixed in a ring shape. The protective sleeve 4 may have a number of turns. In this way, a relatively long catheter 2 may also be arranged advantageously in a space-saving manner. Furthermore, a card 45 may be fixed to the protective sleeve 4, on which card technical information relating to the catheter 2 is displayed (so-called compliance data card).

The solution according to the invention reduces the risk of incorrect manipulation when removing a catheter from a protective device by allowing automatic removal of the cap 30. This results in a beneficial saving of time and increased safety for the patient. In addition, a catheter 2 which has been completely removed from the protective sleeve 4 cannot be repositioned in it.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A protective device for an elongate catheter carrying a functional element on a distal end portion of the catheter, the protective device comprising:
    a protector configured to be arranged on the distal end portion of the catheter such that the functional element is surrounded by the protector, and
    a protective sleeve surrounding an interior configured to accept the catheter and the protector arranged thereon, wherein
    the protective sleeve has at least one projection on an inner side of the protective sleeve facing the interior of the protective sleeve, which projection is configured to retain the protector when the catheter together with the protector of the protective sleeve and the catheter is withdrawn from the protective sleeve such that the protector is pulled off the distal end portion of the catheter.

2. The protective device according to claim 1, wherein the protector comprises a cap having an interior configured to receive the distal end portion of the catheter and the functional element arranged thereon.

3. The protective device according to claim 2, wherein the cap has a funnel-shaped opening, through which the distal end portion of the catheter is insertable into the interior of the cap.

4. The protective device according to claim 3, wherein the protector is configured such that, when the catheter is withdrawn from the protective sleeve, an edge area of the opening of the cap hits against the at least one projection, so that the protector is pulled off the distal end portion of the catheter.

5. The protective device according to claim 1, wherein the at least one projection comprises a rounding.

6. The protective device according to claim 1, wherein the protector comprises a hook arranged at a distal portion of the cap, the hook being configured to hit against the at least one projection when the catheter is withdrawn from the protective sleeve, so that the protector is pulled off the distal end portion of the catheter.

7. The protective device according to claim 1, wherein the at least projection is formed by a movable wing designed to be moved by the protector sitting on the catheter from a disengaged position to an engaged position when the catheter is inserted into the interior of the protective sleeve and to return to the disengaged position after passing the protector.

8. The protective device according to claim 1, wherein the at least one projection is arranged in a proximal portion of the protective sleeve, the proximal portion having an opening of the protective sleeve, via which the catheter is insertable into the interior of the protective sleeve with the protector in front.

9. The protective device according to claim 1, wherein the protective sleeve is arranged in a ring shape or is arrangeable in a ring shape.

10. The protective device according to claim 1, wherein the protector comprises an elongate element, configured to be disposed in a lumen of the catheter when the protector is disposed as intended on the distal end portion of the catheter.

11. The protective device according to claim 10, wherein the elongate element projects from an inner side facing the interior of the cap.

12. The protective device according to claim 3, comprising an elongate element configured to be disposed in a lumen of the catheter, wherein the elongate element protrudes through the opening of the cap from the interior of the cap.

13. The protective device according to claim 10, wherein the elongate element comprises a wire.

14. The protective device according to claim 11, wherein the elongate element projects from a distal portion of the inner side of the cap.

* * * * *